United States Patent [19]

Schwarz et al.

[11] Patent Number: 5,149,522

[45] Date of Patent: Sep. 22, 1992

[54] CLEAR HAIR AND BODY CLEANSING COMPOSITION

[75] Inventors: Horst Schwarz, Seeheim; Hans Hölzel, Fränkisch-Crumbach, both of Fed. Rep. of Germany

[73] Assignee: Wella Aktiengesellschaft, Darmstadt, Fed. Rep. of Germany

[21] Appl. No.: 634,171

[22] PCT Filed: May 8, 1990

[86] PCT No.: PCT/EP90/00742

§ 371 Date: Dec. 18, 1990

§ 102(e) Date: Dec. 18, 1990

[87] PCT Pub. No.: WO90/15589

PCT Pub. Date: Dec. 27, 1990

[30] Foreign Application Priority Data

Jun. 16, 1989 [DE] Fed. Rep. of Germany ....... 3919669

[51] Int. Cl.⁵ .......................... A61K 7/06; A61K 7/48; C11D 9/32
[52] U.S. Cl. ...................................... 424/70; 424/401; 424/71; 252/108; 252/121
[58] Field of Search ............. 424/70, 71, 401; 252/108, 121

[56] References Cited

U.S. PATENT DOCUMENTS 4,752,467 6/1988 Konrad et al. .................. 424/70
4,820,447 4/1989 Medcalf, Jr. et al. .......... 252/121 X
4,946,618 8/1990 Knochel et al. ................ 252/108 X

*Primary Examiner*—Thurman K. Page
*Attorney, Agent, or Firm*—Michael J. Striker

[57] ABSTRACT

The clear aqueous hair and body cleansing composition contains 0.1 to 50 percent by weight lauryl alcohol diglycol ether sulfate and a combination of (A) poly[N-[3-(dimethylammonium)propyl]-N'-[3-(ethylene oxyethylene dimethylammonium)propyl]urea dichloride] and (B) a sulfosuccinate and remains clear when it is thickened with suitable physiologically tolerated salts.

This hair and body cleansing composition produces an outstanding ease of combing and a soft, natural feel of the hair and ensures a pleasant, groomed feeling of the skin and a soft, smooth skin.

14 Claims, No Drawings

CLEAR HAIR AND BODY CLEANSING COMPOSITION

BACKGROUND OF THE INVENTION

The invention relates to a hair and body cleansing composition and, more particularly, to a clear aqueous hair and body cleansing composition which can be thickened with a suitable inorganic salt and is based on lauryl alcohol diglycol ether sulfate or a mixture of surfactants containing lauryl alcohol diglycol ether sulfate.

In addition to the surfactants which bring about the cleansing effect, hair and body cleansing compositions conventionally contain additives for the care of hair and skin therefore these additives are supposed to ensure that the hair be combable when wet as well as when dry, that it have reduced static electricity and a soft and natural feel. In addition, the use of these compositions is supposed to produce a pleasant and groomed feeling of the skin. Skin treated in this manner is supposed to feel smooth and soft to the touch.

It is known to use cationic polymers, e.g. cationic cellulose derivatives, cationic chitosan derivatives or quaternary ammonium salts as conditioning agents in hair and body cleansing compositions.

The use of cationic polymers in compositions for the cleansing of the hair facilitates the untangling of hair treated with the composition, as well as further treatment of the hair, and imparts bounce and luster to the hair. In addition, the body cleansing compositions containing cationic polymers produce a pleasant and groomed feeling of the skin. Certain polyquaternary ammonium salts, for example, produce a powerful conditioning effect on the skin and hair.

In spite of the very good grooming action of the polyquaternary ammonium salts, their use in the production of clear hair and body cleansing compositions has previously been limited, since adding them to the hair and body cleansing compositions containing the conventional anionic surfactants leads to cloudiness and accordingly prevents the production of clear products. Thus, for example, insoluble cloudiness develops when alkyl ether sulfate and polyquaternary ammonium salts are used simultaneously in aqueous solution (Comparison Example 3, Table 1). If a mixture of alkyl ether sulfate and an amphoteric surfactant, e.g. fatty acid alkylamido betaine, is used as a surfactant foundation for hair and body cleansing compositions, an added polyquaternary ammonium salt remains clear in solution (Comparison Example 11, Table 1). However, if the attempt is made to thicken this clear surfactant solution with a suitable inorganic salt, e.g. sodium chloride, precipitations occur (Comparison Example 9, Table 1).

A bath and shower cleansing composition which contains a certain polyquaternary ammonium salt in addition to sulfosuccinates and whose viscosity was adjusted with sodium chloride, has been described by T. Schoenberg (T. Schoenberg, "Formulating Mild Foaming Bath Products", Cosmetics and Toiletries, 100 (5), 53-58 (1985). However, the bath and shower cleansing composition described in the latter is a cloudy product.

SUMMARY OF THE INVENTION

Therefore, there is a need for a clear, aqueous hair and body cleansing composition based on lauryl alcohol diglycol ether sulfate, which possesses good hair and skin grooming properties and can be thickened with suitable inorganic salts.

According to the present invention the problem is solved in an outstanding manner by a clear aqueous hair and body cleansing composition containing 0.1 to 50 percent by weight lauryl alcohol diglycol ether sulfate which is characterized in that it contains a combination of (A) poly[N-[3-(dimethylammonium)propyl]-N'-[3-(ethylene oxyethylene dimethylammonium)propyl]urea dichloride]and
(B) a sulfosuccinate.

The hair treated with the hair cleansing composition, according to the invention, is easily combable in both the wet and the dry state, has reduced static electricity and a soft, natural feel.

The skin treated with the skin cleansing composition, according to the invention, feels soft and smooth to the touch. The skin cleansing composition gives the user a pleasant and groomed feeling.

The new hair and body cleansing composition contains the lauryl alcohol diglycol ether sulfate either as sole surfactant or in combination with other surfactants suitable for this purpose.

The following are mentioned by way of example as surfactants suitable for the new hair and body cleansing composition:

a) the anionic, surface-active agents such as alkali-, alkaline earth-, ammonium- or alkanol amine salts of alkane sulfonates, alkyl sulfates and alkyl ether sulfates, $C_{12}$ to $C_{18}$ -alkyl- and particularly $C_{12}$ to $C_{14}$ -alkyl sulfate sodium salts or -triethanolamine salts, sodium- or triethanol amine salts of lauryl- or tetradecyl ether sulfates, and polyether carboxylic acids;

b) the nonionic surface-active agents such as ethoxylated fatty alcohols with 12 to 18 carbon atoms, e.g. with up to 40 moles ethylene oxide per mole of fatty alcohol ethoxylated lauryl-, tetradecyl-, cetyl-, oleyl-, and stearyl alcohols, alone or in combination; the fatty alcohols of ethoxylated lanolin or ethoxylated lanolin; polyglyceryl ether of saturated or unsaturated fatty alcohols, and alkylphenols with 8 to 30 carbon atoms in the alkyl group and 1 to 10 glyceryl units in the molecule; fatty acid alkanol amides and ethoxylated sorbitane fatty acid esters;

c) the cationic surface-active agents such as dilauryldimethyl ammonium chloride, the chlorides or bromides of alkyl dimethylbenzyl ammonium, the alkyl trimethyl ammonium salts, e.g. cetyl trimethyl ammonium chloride or bromide, tetradecyl trimethyl ammonium chloride or bromide, alkyl dimethyl hydroxyethyl ammonium chlorides or bromides, dialkyl dimethyl ammonium chlorides or bromides, alkylpyridinium salts, e.g. lauryl- or cetylpyridinium chloride, alkyl amide ethyl trimethyl ammonium ether sulfates, imidazoline derivatives, compounds with a cationic character such as amino oxides, e.g. alkyl dimethyl amino oxides or alkyl aminoethyl dimethylamino oxides;

d) the amphoteric or zwitterionic surface-active agents such as the carboxyl derivatives of imidazole, N-alkyl betaines, N-alkylamino betaines, N-alkyl sulfobetaines, N-alkylamino propionates, alkyl dimethyl ammonium acetates, $C_{12}$ to $C_{18}$ -alkyl dimethyl carboxymethyl ammonium salts and fatty acid alkylamido betaines, e.g. dimethyl carboxymethylene propylene amido stearate betaine.

The poly[N-[3-(dimethylammonium)propyl]-N'-[3-(ethylene oxyethylene dimethylammonium)propyl]urea dichloride (A), which has a polymerization coefficient of 4 to 8, preferably 6, and is marketed e.g. by the name Mirapol ®A 15 by Miranol Chemical Company, Inc., is contained in the composition, according to the invention, is a quantity of 0.1 to 5 percent by weight, preferably 0.5 to 1.5 percent by weight.

The sulfosuccinate of component (B) is contained in the hair and skin cleansing composition, according to the invention, in a quantity of 1 to 15 percent by weight, preferably 5 to 15 percent by weight.

All sulfosuccinates suitable for use in hair and skin cleansing compositions can be considered. Such sulfosuccinates are described e.g. in G.A. Nowak, "Cosmetic Preparations" [Die kosmetischen Präparate], second edition pages 227-229, Verlag für chemische Industrie H. Ziolkowsky KG, Augsburg (1984).

The sulfosuccinate is preferably the disodium salt of the coconut fatty acid isopropanolamide semiester of the sulfosuccinic acid containing four oxyethylene units or the disodium salt of a lauryl alcohol semiester of sulfosuccinic acid containing one to four oxyethylene units.

The problem upon which the present invention is based is solved in a particularly favorable manner, when a betaine surfactant is contained as additional surfactant in the composition according to the invention. All betaine surfactants suitable for use in hair and skin cleansing compositions can come under consideration. The cocamidopropyl betaine is particularly preferred. Other suitable betaine surfactants are described e.g. in H. Janistyn, "Handbook of Cosmetics and Scents" [Handbuch der Kosmetika und Reichstoffe], volume 1, page 989, Dr. A. Hüthig Verlag, Heidelberg (1975).

The betaine surfactant can be contained in the composition, according to the invention, in a quantity of 0.1 to 5 percent by weight, preferably in a quantity of 1 to 3 percent by weight.

The clear aqueous hair and body cleansing composition, according to the invention, can contain a physiologically tolerated salt, e.g. sodium sulfate, potassium chloride or sodium chloride, preferably sodium chloride, in order to adjust the viscosity without cloudiness or precipitation occurring in the new composition. The viscosity of the hair and body cleansing composition is 200 to 5000 mPa.s (milli-Pascal seconds), preferably 1000 to 3000 mPa.s. The physiologically tolerated salt is used in a quantity of approximately 0.1 to 6 percent by weight depending on the desired viscosity.

Of course, the composition, according to the invention, can also contain conventional cosmetic additives in addition to the aforementioned components, e.g. perfume oils in a quantity of approximately 0.5 to 5.0 percent by weight, thickeners such as coconut fatty acid diethanol amide in a quantity of approximately 0.5 to 10.0 percent by weight, thinning agents such as 1,2-propylene glycol or ethoxylated sorbitane monolaurate in a quantity of approximately 0.5 to 5.0 percent by weight, buffers such as sodium citrate or sodium phosphate, in a quantity of approximately 0.1 to 1.0 percent by weight, solubilizers such as e.g. ethoxylated, possibly hydrogenated castor oil, in a quantity of approximately 0.1 to 1.0 percent by weight, as well as dyestuffs such as fluorescein sodium salt in a quantity of approximately 0.1 to 1.0 percent by weight. Moreover, it can contain moisturizers, light-protection agents, antioxidants, complexing agents and anti-dandruff ingredients.

Other conventional components known for such compositions, which can be contained in the new composition, are described e.g. in H. Janistyn, "Handbook of Cosmetics and Scents" [Handbuch der Kosmetika und Reichstoffe], volume 3, pages 228-284 and 442-462 (1973), as well as in K. Schrader, "Foundations and Formulas of Cosmetics" [Grundlagen und Rezepturen der Kosmetika], pages 375-401 and 445-455 (1979), and G. A. Nowak, "Cosmetic Preparations" [Die kosmetischen Präparate], pages 227-229 (1975).

The following examples explain the subject matter of the invention in more detail without limiting it to the examples.

EXAMPLES

EXAMPLE 1

HAIR WASHING COMPOSITION

| | |
|---|---|
| 40.00 g | lauryl alcohol diglycol ether sulfate, sodium salt (28 percent aqueous solution) |
| 0.70 g | poly[N-[3-(dimethylammonium)propyl]-N'-[3-(ethylene oxyethylene dimethylammonium)propyl]urea dichloride] (polymerization coefficient = 6, 64 percent aqueous solution) |
| 5.00 g | disodium salt of the coconut fatty acid isopropanolamide semiester of the sulfosuccinic acid containing four oxyethylene units (50 percent aqueous solution) |
| 4.20 g | sodium chloride |
| 50.10 g | water |
| 100.00 g | |

The viscosity of the preceding clear composition is 950 mPa.s, measured at 30 degrees Celsius with a Haake viscosity scale with the use of bar II and a support weight of 5 g.

The hair washed with the described hair washing composition is easily combable in the wet and dry state, has reduced static electricity and a soft, natural feel.

EXAMPLE 2

SHOWER BATH

| | |
|---|---|
| 35.00 g | lauryl alcohol diglycol ether sulfate, sodium salt (28 percent aqueous solution) |
| 7.00 g | cocamidopropyl betaine (30 percent aqueous solution) |
| 1.20 g | poly[N-[3-(dimethylammonium)propyl]-N'-[3-(ethylene oxyethylene dimethylammonium)propyl]urea dichloride] (polymerization coefficient = 6, 64 percent aqueous solution) |
| 8.00 g | disodium salt of a lauryl alcohol semiester of the sulfosuccinic acid containing one to four oxyethylene units |
| 1.60 g | sodium chloride |
| 47.20 g | water |
| 100.00 g | |

The viscosity of the preceding clear composition is 1350 mPa.s, measured at 30 degrees Celsius with a Haake viscosity scale with the use of bar II and a support weight of 5 g. The shower bath, according to the invention, leaves behind a pleasant and groomed feeling of the skin. The skin feels smooth and soft to the touch.

COMPARISON EXAMPLES 3-11

Table 1 shows the cloudiness of the hair and body cleansing composition, not according to the invention, containing polyquaternary ammonium salts before and after thickening with sodium chloride compared with the compositions according to the invention.

TABLE 1

| | 3 | 4 | 5 |
|---|---|---|---|
| lauryl alcohol diglycol ether sulfate, sodium salt (28 percent aqueous solution) | 35.0 | 35.0 | 35.0 |
| cocamidopropyl betaine (30 percent aqueous solution) | — | — | — |
| poly[N-[3-(dimethylammonium)-propyl]-N'-[3-(ethylene oxyethylene dimethylammonium)-propyl]urea dichloride] (polymerization coefficient = 6, 64 percent aqueous solution) | 1.0 | 1.0 | 1.0 |
| disodium salt of a lauryl alcohol semiester of the sulfosuccinic acid containing one to four oxyethylene units | — | — | 5.0 |
| disodium salt of the coconut fatty acid isopropanolamide semiester of the sulfosuccinic acid containing four oxyethylene units | — | — | — |
| sodium chloride | — | 2.0 | — |
| water | 64.0 | 62.0 | 59.0 |
| | flaky precipitate | flaky precipitate | clear |

| | 6 | 7 | 8 |
|---|---|---|---|
| lauryl alcohol diglycol ether sulfate, sodium salt (28 percent aqueous solution) | 35.0 | 40.0 | 40.0 |
| cocamidopropyl betaine (30 percent aqueous solution) | — | — | — |
| poly[N-[3-(dimethylammonium)-propyl]-N'-[3-(ethylene oxyethylene dimethylammonium)-propyl]urea dichloride] (polymerization coefficient = 6, 64 percent aqueous solution) | 1.0 | 1.0 | 1.0 |
| disodium salt of a lauryl alcohol semiester of the sulfosuccinic acid containing one to four oxyethylene units | 10.0 | — | — |
| disodium salt of the coconut fatty acid isopropanolamide semiester of the sulfosuccinic acid containing four oxyethylene units | — | 5.0 | 5.0 |
| sodium chloride | 2.0 | — | 2.0 |
| water | 52.0 | 54.0 | 52.0 |
| | clear | clear | clear |

| | 9 | 10 | 11 |
|---|---|---|---|
| lauryl alcohol diglycol ether sulfate, sodium salt (28 percent aqueous solution) | 35.0 | 35.0 | 35.0 |
| cocamidopropyl betaine (30 percent aqueous solution) | 5.0 | 5.0 | 5.0 |
| poly[N-[3-(dimethylammonium)-propyl]-N'-[3-(ethylene oxyethylene dimethylammonium)-propyl]urea dichloride] (polymerization coefficient = 6, 64 percent aqueous solution) | 1.0 | 1.0 | 1.0 |
| disodium salt of a lauryl alcohol semiester of the sulfosuccinic acid containing one to four oxyethylene units | — | 5.0 | — |
| disodium salt of the coconut fatty acid isopropanolamide semiester of the sulfosuccinic acid containing four oxyethylene units | — | — | — |
| sodium chloride | 2.0 | 2.0 | — |
| water | 57.0 | 52.0 | 59.0 |
| | milky | clear | clear |

The results of the Comparison Examples 3–11 show that in the case of the preparations thickened with sodium chloride a clear composition is only obtained when the composition is composed according to the invention (compare Examples 6, 8 and 10).

COMPARISON EXAMPLES 12 and 13

Table 2 shows that if the poly[N-[3-dimethylammonium)-propyl]-N'-[3-(ethylene oxyethylene dimethylammonium)-propyl]urea dichloride], according to the invention, e.g. as marketed by Miranol Chemical Company, Inc., New Jersey, under the commercial name Mirapol ® A15, is substituted in the same quantity (with respect to the active substance) in the Comparison Examples 6 and 8 by a copolymer of dimethyl diallyl ammonium chloride and acrylamide, e.g. as marketed by Merck & Co., Inc., New Jersey, under the commercial name Merquat ® 550, no clear compositions are obtained:

TABLE 2

| | 12 | 13 |
|---|---|---|
| lauryl alcohol diglycol ether sulfate, sodium salt (28 percent aqueous solution) | 35.0 | 40.0 |
| cocamidopropyl betaine (30 percent aqueous solution) | — | — |
| copolymer of dimethyl diallyl ammonium chloride and acrylamide (8 percent aqueous solution) | 8.0 | 8.0 |
| disodium salt of a lauryl alcohol semiester of the sulfosuccinic acid containing one to four oxyethylene units | 10.0 | — |
| disodium salt of the coconut fatty acid isopropanolamide semiester of the sulfosuccinic acid containing four oxyethylene units | — | 5.0 |
| sodium chloride | 2.0 | 2.0 |
| water | 45.0 | 45.0 |
| | cloudy | cloudy |

All percentages indicated in the present Application refer to percent by weight.

We claim:

1. Clear aqueous hair and body cleansing composition consisting essentially of 0.1 to 50 percent by weight lauryl alcohol diglycol ether sulfate, a poly[N-[3-(dimethylammonium)propyl]-N'-[3-(ethyleneoxyethylenedimethylammonium)propyl[urea dichloride], a sulfosuccinate and water.

2. Composition according to claim 1, wherein said poly[N-[3-(dimethylammonium)propyl]-N'-[3-(ethylene oxyethylenedimethylammonium)propyl]urea dichloride] is contained in a quantity of 0.1 to 5 percent by weight.

3. Composition according to claim 1, wherein said sulfosuccinate is contained in a quantity of 1 to 15 percent by weight.

4. Composition according to claim 1, wherein said sulfosuccinate is selected from the group consisting of disodium salts of coconut fatty acid isopropanolamide semihesters of sulfosuccinic acid containing four oxyethylene units and disodium salts of lauryl alcohol semihesters of sulfosuccinic acid containing one to four oxyethylene units.

5. Clear aqueous hair and body cleansing composition consisting essentially of 0.1 to 50 percent by weight lauryl alcohol diglycol ether sulfate, a poly[N-[3-(dimethylammonium)propyl]-N'-[3-(ethyleneoxyethylenedimethylammonium)propyl[urea dichloride], a sulfosuccinate, a salt for adjusting composition viscosity and water.

6. Composition according to claim 5, wherein the salt is sodium chloride.

7. Composition according to claim 1, having a viscosity of 200 to 5000 mPa.s(milli-Pascal seconds).

8. Clear aqueous hair and body cleansing composition consisting essentially of 0.1 to 50 percent by weight lauryl alcohol diglycol ether sulfate, from 0.1 to 5 percent by weight of a poly[N-[3-(dimethylammonium)propyl]-N'-[3-(ethyleneoxyethylenedimethylammonium)propyl[urea dichloride], from 1 to 15% by weight of a sulfosuccinate, a betaine surfactant, a salt for viscosity adjustment in an amount such that said composition has a viscosity from about 200 to 5000 mPa.s(milli-Pascal seconds) and water.

9. Composition according to claim 8, wherein the betaine surfactant is cocamidopropyl betaine.

10. Composition according to claim 8, wherein the betaine surfactant is contained in a quantity of 0.1 to 5 percent by weight.

11. Composition according to claim 8, wherein said salt is selected from the group consisting of sodium sulfate, potassium chloride and sodium chloride.

12. Clear aqueous hair and body cleansing composition consisting essentially of 0.1 to 50 percent by weight lauryl alcohol diglycol ether sulfate, a poly[N-[3-(dimethylammonium) propyl]-N'-[3-(ethyleneoxyethylenedimethylammonium)propyl[urea dichloride], a sulfosuccinate; another surfactant selected from the group consisting of anionic surface-active agents, nonionic surface-active agents, cationic surface-active agents and amphoteric surface-active agents; and water.

13. Clear aqueous hair and body cleansing composition consisting essentially of 0.1 to 50 percent by weight lauryl alcohol diglycol ether sulfate, a poly[N-[3-(dimethylammonium) propyl]-N'-[3-(ethyleneoxyethylenedimethylammonium)propyl[urea dichloride], a sulfosuccinate; another surfactant selected from the group consisting of anionic surface-active agents, nonionic surface-active agents, cationic surface-active agents and amphoteric surface-active agents; an inorganic salt for viscosity adjustment present in an amount such that said composition has a viscosity from about 200 to 5000 mPa.s(milli-Pascal seconds) and water.

14. Clear aqueous hair and body cleansing composition consisting essentially of 0.1 to 50 percent by weight lauryl alcohol diglycol ether sulfate; from 0.1 to 5 percent by weight of an poly[N-[3-(dimethylammonium)-propyl]-N'-[3-(ethyleneoxyethylenedimethylammonium)propyl[urea dichloride]; 1 to 15% by weight of a sulfosuccinate, another surfactant; at least one cosmetic additive selected from the group consisting of perfume oils, thickeners, thinning agents, buffers, solubilizers, dyestuffs, moisturizers, light-protecting agents, antioxidants, complexing agent and anti-dandruff ingredients; 0.1 to 6% by weight of a salt for viscosity adjustment; and water.

* * * * *